(12) United States Patent
Lemberg et al.

(10) Patent No.: US 8,496,696 B2
(45) Date of Patent: Jul. 30, 2013

(54) SYSTEM AND METHOD FOR MICROABLATION OF TISSUE

(75) Inventors: Vladimir Lemberg, Santa Clara, CA (US); Vitali Epshtein, Binyamina (IL); Yoni Iger, Haifa (IL); John Lee Pannell, Knoxville, TN (US)

(73) Assignee: Lumenis Ltd., Yokneam, IL (US)

( * ) Notice: Subject to any disclaimer, the term of this patent is extended or adjusted under 35 U.S.C. 154(b) by 1457 days.

(21) Appl. No.: 11/730,017

(22) Filed: Mar. 29, 2007

(65) Prior Publication Data

US 2008/0071258 A1 Mar. 20, 2008

Related U.S. Application Data (60) Provisional application No. 60/791,194, filed on Apr. 12, 2006, provisional application No. 60/850,628, filed on Oct. 11, 2006, provisional application No. 60/832,964, filed on Jul. 25, 2006.

(51) Int. Cl.
*A61N 5/06* (2006.01)

(52) U.S. Cl.
USPC .......................................................... 607/89

(58) Field of Classification Search
USPC ........................................ 128/898; 606/2–19
See application file for complete search history.

(56) References Cited

U.S. PATENT DOCUMENTS

| 4,408,602 | A |   | 10/1983 | Nakajima |   |
|---|---|---|---|---|---|
| 5,713,902 | A |   | 2/1998 | Friedl |   |
| 5,843,079 | A | * | 12/1998 | Suslov | 606/43 |
| 5,908,417 | A |   | 6/1999 | Miller et al. |   |
| 5,957,915 | A |   | 9/1999 | Trost |   |
| 6,027,501 | A | * | 2/2000 | Goble et al. | 606/41 |
| 6,099,522 | A |   | 8/2000 | Knopp et al. |   |
| 6,110,195 | A |   | 8/2000 | Xie et al. |   |
| 6,117,130 | A | * | 9/2000 | Kung | 606/28 |
| 6,143,018 | A | * | 11/2000 | Beuthan et al. | 607/88 |
| 6,152,918 | A |   | 11/2000 | Padilla et al. |   |
| 6,328,733 | B1 |   | 12/2001 | Trost |   |
| 6,482,199 | B1 |   | 11/2002 | Neev |   |
| 6,595,987 | B1 |   | 7/2003 | Negus et al. |   |
| 6,763,836 | B2 |   | 7/2004 | Tasto et al. |   |
| 6,881,212 | B1 |   | 4/2005 | Clement et al. | 606/9 |
| 6,902,562 | B1 |   | 6/2005 | Negus et al. |   |
| 2002/0045811 | A1 |   | 4/2002 | Kittrell et al. |   |
| 2002/0120260 | A1 |   | 8/2002 | Morris et al. |   |

(Continued)

FOREIGN PATENT DOCUMENTS

| EP | 1627662 | 2/2006 |
|---|---|---|
| WO | 9113652 | 9/1991 |

(Continued)

OTHER PUBLICATIONS

International Search Report for PCT/US07/07829, mailed Mar. 13, 2008.

(Continued)

*Primary Examiner* — Sam Yao
*Assistant Examiner* — John R Downey
(74) *Attorney, Agent, or Firm* — Fogg & Powers LLC (57) ABSTRACT

The present invention generally relates to the field of laser treatment of tissue, and particularly, to a system and method for creating microablated channels in skin. The present invention is more particularly directed to treating subsurface tissue through the created channels.

9 Claims, 3 Drawing Sheets

U.S. PATENT DOCUMENTS

| | | |
|---|---|---|
| 2002/0161357 A1 | 10/2002 | Anderson et al. |
| 2002/0183724 A1 | 12/2002 | Neev |
| 2003/0083607 A1* | 5/2003 | Bobo, Jr. .................... 604/20 |
| 2003/0095266 A1 | 5/2003 | Detalle et al. |
| 2003/0199859 A1 | 10/2003 | Alshuler et al. |
| 2003/0216719 A1 | 11/2003 | Debenedictis et al. |
| 2004/0143248 A1 | 7/2004 | Marchitlo et al. |
| 2004/0195221 A1 | 10/2004 | Haglund, Jr. et al. |
| 2004/0230258 A1 | 11/2004 | Altshuler et al. |
| 2005/0049582 A1 | 3/2005 | DeBenedictis et al. |
| 2005/0070896 A1 | 3/2005 | Daniel et al. .................... 606/50 |
| 2005/0154380 A1 | 7/2005 | DeBenedictis et al. |
| 2006/0058712 A1 | 3/2006 | Altshuler et al. |
| 2006/0079816 A1 | 4/2006 | Barthe et al. |
| 2006/0095103 A1* | 5/2006 | Eggers et al. .................... 607/96 |
| 2006/0149223 A1 | 7/2006 | Hwang et al. |
| 2006/0217695 A1 | 9/2006 | DeBenedictis et al. |
| 2006/0241442 A1* | 10/2006 | Barthe et al. .................... 600/439 |
| 2006/0271028 A1 | 11/2006 | Altshuler et al. |
| 2007/0118098 A1 | 5/2007 | Tankovich |
| 2007/0239236 A1 | 10/2007 | Manstein |
| 2007/0264288 A1 | 11/2007 | Manstein |
| 2008/0071258 A1 | 3/2008 | Lemberg et al. |
| 2009/0112192 A1 | 4/2009 | Barolet et al. |

FOREIGN PATENT DOCUMENTS

| | | |
|---|---|---|
| WO | 9726830 | 7/1997 |
| WO | 9938572 | 8/1999 |
| WO | 02090036 | 11/2002 |

OTHER PUBLICATIONS

European Patent Office, "Office Action", Jun. 7, 2011, Published in: EP.

European Patent Office, "Office Action", Feb. 13, 2012, Published in: EP.

Choi et al., "Analysis of Thermal Relaxation During Laser Irradiation of Tissue", "Lasers in surgery and Medicine", Oct. 2001, pp. 351-359, vol. 29.

Laubach et al, "Skin Responses to Fractional Photothermolysis", "Lasers in Surgery and Medicine issue 2", Feb. 2006, pp. 142-149, vol. 38, Publisher: Wiley-Liss, Inc.

Manstein et al., "Fractional Photothermolysis: A New Concept for Cutaneous Remodeling Using Microscopic patterns of Thermal Injury", "Lasers in Surgery and Medicine issue 5", Jun. 2004, pp. 426-438, vol. 34.

McKenzie, "A Three-Zone Model of Soft-Tissue Damage by a CO2 Laser", "Phys. Med. Biol.", Feb. 19, 1986, pp. 967-983, vol. 31, No. 9, Publisher: The Institute of Physics.

* cited by examiner

SYSTEM AND METHOD FOR MICROABLATION OF TISSUE

CROSS REFERENCE TO RELATED APPLICATIONS

This application claims the benefit of U.S. Ser. No. 60/791,194, filed on Apr. 12, 2006 (and entitled: System, Method and Apparatus For Laser Treatment of Tissue), U.S. Ser. No. 60/850,628, filed on Oct. 11, 2006 (and entitled: A Novel Microablative Device) and U.S. Ser. No. 60/832,964, filed on Jul. 25, 2006 (and entitled: System, Method and Apparatus For Laser Treatment of Tissue) which are incorporated in their entirety herein by reference.

BACKGROUND OF THE INVENTION

1. Field of the Invention

The present invention generally relates to the field of laser treatment of tissue, and particularly, to a system and method for creating microablated channels in skin. The present invention is more particularly directed to treating subsurface tissue through the created channels. By treating subsurface tissue through uniquely created channels, skin may be treated with heretofore unrealized results.

2. Description of the Related Art

Skin is primarily made of an outer layer, or epidermis, that has a depth of approximately 100/an from the outer surface of the skin and an inner layer, or dermis, that has depth of approximately 3000 fm from the outer surface of the skin. As used herein, "dermal tissue" or "skin" refers to both the dermis and epidermis layers.

There is ongoing demand for procedures to improve skin defects. Such improvements include reducing wrinkles, reducing dyschromia (a variety of abnormalities or irregularities of skin color resulting from, inter alia, irregular pigment distribution, dilated blood vessels, etc.) and etc. A wide variety of skin treating techniques have been introduced in recent years for attempting to achieve this objective. The skin treating techniques that have been employed may be generally categorized into two general types of treatment: ablative laser skin resurfacing ("LSR") and non-ablative collagen remodeling ("NCR"). LSR generally may result in fairly extensive thermal damage to either the epidermis and/or the dermis. NCR, on the other hand, is designed to avoid thermal damage of the epidermis.

Nevertheless, LSR is an effective laser treatment for treating skin. A typical LSR procedure comprises thermally damaging a region of the epidermis and a corresponding lower region of the dermis for promoting wound healing. Electromagnetic energy 120 is directed towards a region of skin, thereby ablating the skin and removing both epidermal tissue and dermal tissue. Combining LSR with a pulsed laser, for example a CO.sub.2 or an Er:YAG laser, is typically referred to as laser resurfacing or ablative resurfacing. This is considered to be an effective treatment protocol photo aged or chronically aged skin, scars, superficial pigmented lesions, stretch marks, and/or superficial skin lesions. Major drawbacks include, however, edema, oozing, and burning discomfort up to the first fourteen (14) days after treatment. Such drawbacks are unacceptable for many patients. A further problem with LSR procedures is that they are relatively painful. Therefore, they generally require an application of a significant amount of analgesia. While LSR of relatively small areas can be performed under local anesthesia, LSR procedures that include relatively large areas frequently require general anesthesia or nerve blockage by multiple anesthetic injections.

Another limitation of LSR is that ablative laser resurfacing generally can not be performed on the patients having dark complexions. Ablation of pigmented epidermis tissue can cause severe cosmetic disfigurement to patients having a dark complexion. Such disfigurement can last from several weeks up to years. This is generally considered to be unacceptable by most patients and physicians. Yet another limitation of LSR is that ablative resurfacing generally has a greater risk of scarring in areas other than the face and result in an increased incidence of an unacceptable scar formation because the recovery from skin injury within these areas is not very effective.

Several NCR techniques have attempted to overcome the aforesaid problems associated with LSR procedures. These techniques may be variously referred to as non-ablative resurfacing, non-ablative subsurfacing, or non-ablative skin remodeling. Such NCR techniques generally use non-ablative lasers, flash lamps, or radio frequency current for damaging the dermal tissue and avoiding damage to the epidermal tissue. NCR techniques apply the concept that it is the thermal damage of the dermal tissues that is thought to induce wound healing. This results in biological repair and the formation of new dermal collagen which in turn can result in decreased photoaging related structural damage. Avoiding the epidermal damage by using NCR techniques may also decrease both the severity and the duration of treatment related side effects, for example, post procedural oozing, crusting, pigment changes, and the incidence of infections.

Treating skin using the NCR method involves heating selective portions of dermal tissue within the dermal layer for inducing wound healing without damaging the epidermis above. By cooling the surface of the skin and focusing electromagnetic energy, for example a laser beam, a selected dermal damaged region can be achieved while leaving the epidermis undamaged. Using non-ablative lasers for damaging the dermis while leaving the epidermis undamaged is common to NCR treatment methods. Generally, using non-ablative lasers result in deeper dermal penetration depths as compared to the ablative lasers than the superficially-absorbed ablative Er:YAG and $CO_2$ lasers used in typical LSR procedures. Further, when NCR techniques are used, they generally do not have the undesirable side effects characteristic of the LSR treatment, such as the risk of scarring or infection. Examples of NCR techniques and apparatus are disclosed by Anderson et al. in U.S. Patent Publication No. 2002/0161357.

Although these NCR techniques may avoid epidermal damage, a major drawback of this method is its limited effectiveness. For example, this is significantly less improvement of photoaged skin or scars after the NCR treatment than when LSR ablative techniques is used. In fact, even when multiple NCR treatments are employed, improvement in the patient's skin is often far below expectations. In addition, improvement is often delayed for several months when a series of treatment procedures are used. Although NCR techniques have been found to be moderately effective for wrinkle removal, they have generally not been found to be effective for dyschromia Another problem with using a NCR technique is the limited the breadth of acceptable treatment parameters for safe and effective treatment of dermatological disorders. This is because NCR procedures generally rely on an optimum coordination of laser energy and cooling parameters. This results in an unfavorable temperature profile in the skin. An unfavorable temperature profile consequently results in either no therapeutic effect on one hand, or scar formation due to the overheating of a relatively large volume of the tissue, on the other.

Although these NCR techniques may avoid epidermal damage, a major drawback of this method is its limited effectiveness. For example, this is significantly less improvement of photoaged skin or scars after the NCR treatment than when LSR ablative techniques are used. In fact, even when multiple NCR treatments are employed, improvement in the patient's skin is often far below expectations. In addition, improvement is often delayed for several months when a series of treatment procedures are used. Although NCR techniques have been found to be moderately effective for wrinkle removal, they have generally not been found to be effective for dyschromia Accordingly, there is now provided with this invention an improved system and method for treating skin that effectively overcomes the aforementioned difficulties and longstanding problems inherent in using either a LSR or a NCR procedure. These problems have been solved in a simple, convenient, and highly effective way by which to treat skin.

SUMMARY OF THE INVENTION

According to one aspect of the invention, a method for treating tissue is disclosed. The method comprises applying electromagnetic radiation to the tissue for ablating a channel therein having a predetermined width and predetermined depth. The method includes non-ablatively heating tissue on the bottom of the channel with electromagnetic radiation and creating a thermal affected zone of predetermined volume proximate said channel.

According to another aspect of the invention, a system for treating tissue, is disclosed which comprises an electromagnetic radiation source and an electromagnetic radiation emitting device for applying the electromagnetic radiation to the tissue for forming a channel therein having a predetermined width, predetermined depth, and a thermal affected zone of predetermined volume proximate said channel.

As will be appreciated by those persons skilled in the art, a major advantage provided by the present invention is full control of: depth of treatment, the amount and placement of heat, and the amount and placement of channels. It is therefore an object of the present invention to rejuvenate skin and reduce wrinkles, scars, dyschromia and other conditions such as melasma and hyperpigmentation. It is another object to provide a channel with or without heat for delivery other therapy (vitamins, drugs, etc). Additional objects of the present invention will become apparent from the following description.

The method and apparatus of the present invention will be better understood by reference to the following detailed discussion of specific embodiments and the attached figures which illustrate and exemplify such embodiments.

DESCRIPTION OF THE DRAWINGS

A specific embodiment of the present invention will be described with reference to the following drawings, wherein.

DESCRIPTION OF THE PREFERRED EMBODIMENT

The following preferred embodiment as exemplified by the drawings is illustrative of the invention and is not intended to limit the invention as encompassed by the claims of this application. A system and method for treating skin is disclosed herein. In skin tissue, for example, proteins such as collagen reside in the dermal layer of the skin. The microchannel disclosed in an embodiment of the present invention may itself target and alter the collagen fibers within the dermis as an effective treatment for wrinkles of the skin. Alternatively, an embodiment of the microchannel disclosed herein may create a passage through which targeted tissue is treated.

Figure 1:
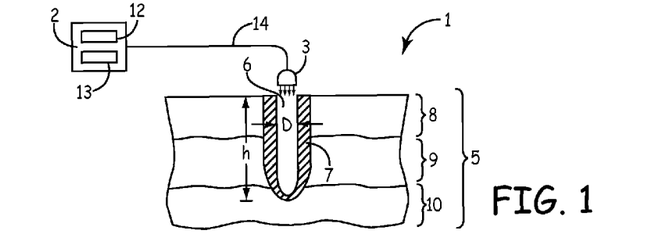
FIG. 1 is a schematic illustration of a microablation method and system in accordance with an embodiment of the invention.

As shown generally in FIG. 1, an embodiment of the present invention provides a system and method for performing microscopic ablation or partial microablation of e.g. tissue, and forming a microchannel through a surface of tissue to treat subsurface tissue. The microchannel may provide access to subsurface tissue targeted for a prescribed treatment, or the microchannel itself may provide a prescribed treatment. In some embodiments of the present invention, the microchannel may produce partial lateral denaturation of proteins (e.g. collagen) within the walls and/or at the bottom of the channel.

According to some embodiments of the invention, a tissue ablation system 1 may include a laser unit 2 and a laser emitting device 3 for ablating a microchannel 6 into a tissue 5, for example, for applying a treatment thereto as will be described below in detail. The microchannel 6 may be, e.g. a column, a well, a hole, or the like, created in the tissue 5 by ablating the tissue 5 by the laser emitting device 3 and the laser beam 4, for example, an ablating laser beam. Microablation of the tissue 5 may result in ablation of the microchannel. Microablation of the tissue may also result in dissipation of heat from the heated and evaporated tissue by the tissue surrounding the resultant microchannel 6. Thus, ablation of the tissue 5, producing the microchannel 6, may result in a thermal affected zone 7 surrounding the walls and/or bottom of the microchannel 6. The thermal affected zone 7 is generally indicative of damaged tissue and of tissue necrosis (the death of cells) in particular. As used herein, "damaged" is defined as inducing cell death in one or more regions of the dermal tissue of interest ("lethal damage"), or stimulating the release of cytokines, heat shock proteins, and other wound healing factors without stimulating necrotic cell death ("sublethal damage").

Selection of the laser beam 4 may also be based on the absorptive qualities of the tissue 5 to be treated. The absorptive properties of the tissue 5 to be treated may dictate or influence the specific type of laser or the characteristics of that laser suitable for a particular treatment for and/or microchannel. For example, certain lasers may reach depths unable to be reached by other types of lasers. As an example, an ablative laser may reach up to any depth required while non-ablative lasers may be unable to penetrate skin below, for example, about 50 .mu.m. Similarly, it may be difficult to reach energy doses with one type of laser that are easily reached with others. Of course, as is well known in the art, if the wavelength is altered, the corresponding absorption level of the skin treatment area will be altered. Therefore, as long as the fluence described herein is maintained for achieving the microablation disclosed herein, different lasers having different characteristics may be used for achieving the same or similar results disclosed.

The microchannel 6 may be characterized by certain parameters, for example, diameter D and depth h. The diameter D of the microchannel and the depth h of the microchannel generally may be controlled by the energy characteristics of the laser. Such energy characteristics include, for example, wavelength, power, and the beam profile of the laser. Characteristics of the beam profile of the laser include, for example, pulse width, pulse duration, and pulse frequency). Furthermore, the profile and volume of the thermal affected zone may be formed by using different laser beam characteristics, such as chosen wavelength, energy of individual pulse or defined sequence of pulses, duration of each pulse, power distribution, shape of the laser spot, and the like, as will be outlined in detail below.

In some embodiments of the invention, the diameter of the ablated microchannel 6 may range from about 10 μm to about 500 μm, preferably in the range from about 50 μm to about 250 μm. Microchannel diameter D may depend on the type of laser used and other parameters, for example, the elasticity of the skin. It has been found that the bottom of the formed microchannel is often conical due to the elastic forces of the skin as well as the power energy distribution of the spot formed by the laser.

The depth of the microchannel may be determined by the attending physician based upon the treatment required or selected by the physician. For example, treatment of collagen (collagen remodeling) typically located at a depth in the range from about 200 μm to about 2 mm from the surface of skin tissue may be desired. Treatment of blood vessels may necessitate a microchannel extending up to approximately 0.5 mm, which is where blood vessels are typically located. The microchannel 6 may therefore be created in accordance with an embodiment of this invention to a predetermined depth h to effect treatment to collagen or blood vessels or any other portion of the dermis selected by the attending physician. According to some embodiments of the present invention, the laser device 4 may produce the microchannel 6 reaching, for example, in the range from about 100 μm to about 3 mm in depth below the surface of the tissue 5.

Any suitable type of laser may be used, for ablating the microchannel, for example, $CO_2$ laser, Er:YAG, Tm:YAG, Tm fiber laser, Er fiber laser, Ho fiber laser, etc. or any other laser type as is well known in the art which may match a predetermined operational parameter such as, for example, optical absorption by tissue and intensity of laser that are strong enough to ablate small volumes with minimal lateral damage. The laser emitting device 3 may therefore be adapted for emitting an ablative laser beam 4 having any suitable power level and/or spot size and/or other associated characteristics. The laser power level may range, for example, in the range from about 0.5 mJ to about 250 mJ. The spot size of the laser beam 4 on the tissue surface may range, for example, in the range from about 10 μm to about 50 μm. For example, a $CO_2$ laser may use a spot size ranging from about 80 μm to about 150 μm for ablative treatment and preferably about 80 μm.

In some embodiments of the present invention, the ablation may be produced by a continuous wave laser, by a single pulse of a laser, or by a series of pulses. The selection of these forms may depend, for example, upon the depth of the microchannel required, the diameter of the microchannel, as well as the size of the thermal affected zone, that is, the width of the lateral damage. In an embodiment using a continuous wave laser, for example, an ablating laser operating in a wavelength of 10.6 nm, the laser emitting device 3 may be operated at a power level of, e.g., in the range from about 1.0 W to about 250 W for a duration of, e.g., in the range from about 0.02 msec to about 500 msec. In an embodiment using a pulsed $CO_2$ laser, for example, a series of, for example, 10 pulses, each having a duration of, for example in the range from about 0.05 msec to about 100 msec may be fired at an energy level of, e.g. in the range from about 0.2 mJ to about 20 mJ. In an embodiment using a pulsed laser, a series of pulses, each having a duration of from about 0.05 msec to about 100 msec may be fired may be fired at an energy level of in the range from about 0.2 mJ to about 20 mJ. In skin, for example, applying a pulsed laser as indicated above may result in a microchannel 6 of a diameter in the range of from about 80 μm to about 100 μm, a depth in the range of from about 300 μm to about 500 μm, and a thermal affected zone of lateral width in the range of from about 20 μm to about 300 μm. Additionally, as described below in an embodiment of the invention, a series of pulses, of pulsed laser may be fired at the tissue 5 to further deepen the microchannel 6, created as identified above. The microchannel 6 may be deepened to a desired depth, preferably to the level of the tissue to be non-ablatively treated. It should be noted that the diameter of the deepened microchannel 6 may be in the same range or different range as the previously created microchannel in the same location.

In some embodiments of the invention, the microablation channel 6 may be sculpted by employing different pulse characteristics of the laser beam. Pulse characteristics of a laser beam, e.g. laser beam 4, may further include different energy profiles. As mentioned above, the depth h of the microchannel and the resulting width of lateral damage and the profile of the thermal affected zone 7 may be controlled by different laser beam characteristics. For example, the laser beam 4 may have characteristics resulting in the thermal affected zone 7 having a substantially constant width (linear profile) 7. It will be recognized that some embodiments of the invention may have a thermal affected zone 7 profile different from the one depicted in FIG. 1. Furthermore, it is now possible to produce a microchannel 6 according to embodiments of the present invention with a minimal thermal affected zone 7, e.g. a width in the range from about 1 μm to about 5 μm with the use of the Er:YAG laser.

In some embodiments of the present invention, the laser unit 2 may include a controller 12 able to control the laser emitting device 3, and an input interface 13 capable of receiving input parameters from user of system 1. Such input parameters may be for defining microablation treatment parameters, for example. User input parameters to the interface 13 may further include the microchannel depth, the spatial location of the microchannel 6 on the tissue surface 1, etc. Parameters may be provided at the input interface 13 by an operator of the system, for example, a physician, or alternatively, through an imager program detailed below. The controller 12 may be able to perform at least one of the following functions, as will be described in more detail below: (a) identifying at least one location for treatment; (b) selecting treatment(s) for each of at least one location; (c) operating a laser and directing mechanism to produce the at least one microablation; and (d) delivering the selected treatment(s) at the at least one site.

Figure 2A:
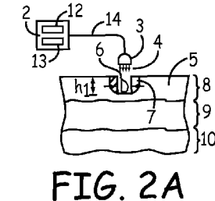
FIGS. 2A, 2B, 2C, and 2D are schematic illustrations of sequential stages of microablation and treatment in accordance with an embodiment of the invention.
Figure 2B:
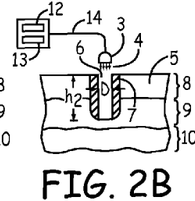
Figure 2C:
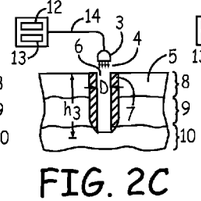
Figure 2D:
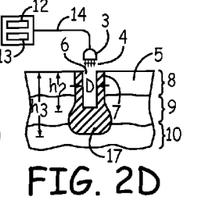

Reference is now made to FIGS. 2A, 2B, 2C, and 2D which schematically illustrate sequential stages of microablation and treatment in accordance with an embodiment of the invention. According to an embodiment of the invention, it may be desirable to apply treatment to tissue which may be, for example, in the hypodermis 10 in a way that substantially maintains the profile of the thermal affected zone throughout the treatment protocol. As it is desirable to minimize the necrosis of tissue at the surface 11, it may be beneficial to apply a plurality of laser pulses onto the tissue 5 in order to reach a depth of treatment area in the hypodermis 10. As illustrated in FIG. 2A, the microchannel 6 created by a first ablative laser pulse, may have the desired thermal affected zone 7, e.g. linear profile of constant width, for example, a minimal width, and may have a depth of h1 that is not sufficiently deep to provide treatment to the hypodermis 10. A second ablative laser pulse may be applied through microchannel 6 of FIG. 2A to deepen the microchannel 6 having a minimal thermal affected zone to a depth h2 into, for example, the dermis 9 of the tissue 5, while maintaining the predetermined minimal thermal affected zone profile, as illustrated in FIG. 2B. Finally, as indicated in FIG. 2C, a third ablative laser pulse may be applied through the microchannel 6 of FIG. 2B to deepen the microchannel 6 having a minimal thermal affected zone 7 further to a depth h3 into the targeted hypodermis layer 10, while maintaining the predetermined thermal affected zone profile 7. Alternatively, if a non-ablative pulse is applied after the profile depicted in FIG. 2B, the profile may appear as depicted in FIG. 2D.

According to some embodiments of the invention, a delay representing a minimum time, e.g. 1 to 100 msec, may pass between each laser pulse, thereby allowing relevant portions of tissue 5 to cool down between each pulse. This delay may be between any succession of laser pulses whether they are ablative or non-ablative. It is preferable to have a delay after an ablative laser pulse. To allow for cooling of tissue 5, the minimum time between pulses may be determined according to, for example, a predetermined tissue relaxation time which may define, e.g. the time required to dissipate a certain amount of heat absorbed by, e.g. the tissue 5, during a laser pulse applied by the laser device 3. The delay may also allow venting of ablative tissue and or gases that may have developed during an ablative pulse of light. Accordingly, if a time of an applied pulse is shorter than the tissue relaxation time and the beam has a top hat profile a very low amount of heat may dissipate through walls of the microchannel 6.

A beam profile that would conform to an inverted top bat may be preferable in some embodiments of the present invention for forming a channel with well defined side walls, minimal microchannel diameter, and a minimal thermal affected zone. Typically, a beam has a Gaussian power distribution across the diameter of its spot. Since the power on the edges of such a spot is less than the power in the center of the spot, it is often difficult to form a straight walled channel or hole. By having a beam profile that has a uniform power distribution across its spot (a top hat profile) it will be easier to form a straight walled channel.

In some embodiments of the invention, upon producing the microchannel and clearing a path to the treatment site, a wide variety of types of treatment may be delivered to the site, as detailed below. In some embodiments, the treatment may be non-ablative laser treatment. Such non-ablative laser treatment may be used, for example, for remodeling collagen. As is more particularly illustrated in FIG. 2D, a non-ablative laser treatment may be delivered to the tissue 5 in the dermis 9 after the microchannel 6 has been created. The path created for the non-ablative heating of the target tissue may follow embodiments of the invention detailed above regarding FIGS. 2A, or 2B and/or 2C. That is, heating of subsurface tissue by a non-ablative laser through the created microchannel may be through a microchannel that was created by one or by more that one ablative pulses. Laser treatment by the laser beam 4 may be applied to the tissue 5 in the dermis 9, whereby the tissue 5 is heated to a temperature below that at which the tissue is ablated though heated to a temperature sufficient to denature collagen, for example, in the range of from about 50° C. to about 67° C. The non-ablative laser beam 4 may further create a thermal affected zone of denatured collagen 17, without tissue ablation, whereby collagen is heated. The collagen thereupon contracts, thus removing wrinkles. The non-ablative laser beam 4 may further be applied to targeted tissue for removing pigmentation, treating blood vessels, and other treatments, as is well known to those skilled in the art.

Accordingly, it will be appreciated that the use of the microchannel 6 of the present invention as a conduit for applying non-ablative heat to targeted subsurface tissue, enables the heating of the subsurface tissue to be treated without excessively damaging non-targeted tissue, for example, the surface tissue. Further, the thermal affected zone may be additionally controlled by having non-ablative heating applications interposed between ablative treatments for creating a larger thermal affected zone 17 deep in the tissue, for example in the dermis 9.

Figure 3A:
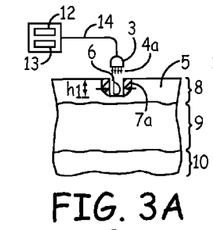
FIGS. 3A, 3B, 3C, and 3D are schematic illustrations of sequential stages of microablation in accordance with an embodiment of the invention.
Figure 3B:
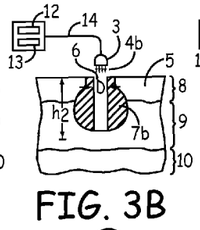
Figure 3C:
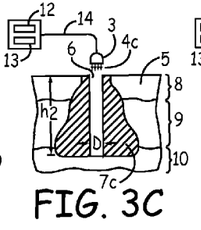
Figure 3D:
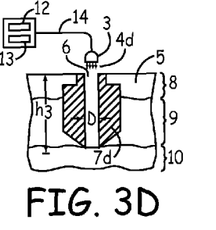

Reference is now additionally made to FIGS. 3A, 3B, 3C, and 3D which schematically illustrate sequential stages of treatment in microablation channels in accordance with embodiments of the invention. In accordance with to some embodiments of the invention, it may be desirable to create a predetermined non-uniform thermal affected zone profile and/or lateral width damaged area along the depth of the channel. In other embodiments of the invention, an area of tissue in the dermis 9 may be, treated for forming a predetermined thermal affected zone having a profile different from the profile of the thermal affected zone in the epidermis 8 near the surface. As is more particularly illustrated in FIG. 3A, the microchannel 6 having a predetermined thermal affected zone and/or profile 7a and a depth h1 may be created by a first ablative laser pulse. As illustrated in FIG. 2D, a second laser non-ablative laser pulse may heat the bottom of the microchannel 6 thereby damaging a spherical area surrounding the bottom of the channel to a depth h3, reaching for example, beyond the dermis 9. This second pulse may have different characteristics than the first pulse, producing a thermal affected zone having a different area and/or profile than the first pulse and resulting in the profile illustrated in FIG. 2D. When a second ablative laser pulse (that is, the third pulse to this treatment area) is applied through the damaged tissue on the bottom of the microchannel, a profile 7b as depicted in FIG. 3B is formed. Thus, FIG. 3B depicts an ablative laser pulse applied subsequent to the non-ablative laser pulse which formed the profile depicted in FIG. 2D. Alternating ablative laser treatment with non-ablative laser treatment may result, for example, in a microchannel having a thermal affected profile as illustrated in FIG. 3C. It will be understood that a microchannel may be produced to any depth and by any number of pulses for creating a series of predetermined thermal affected zones that may vary along the depth of the microchannel. In this way, a predetermined thermal affected zone profile along the microchannel 6 is formed. It is thus possible to build a variety of predetermined thermal affected zone areas and/or profiles along the wall and/or the bottom of the microablated channel, using a sequence of pulses with different parameters (e.g. energy and duration or wavelength) and employing the natural thermal conductivity of tissue. For example, in another embodiment of the invention, an ablative laser pulse applied to the tissue 5 may have characteristics producing a thermal affected zone having an area and/or profile 7$d$ as illustrated in FIG. 3D. The thermal affected zone 7$d$ in FIG. 3D illustrates that the thermal affected zone area may decrease along the depth of the channel, according to predetermined laser beam parameters. Of course, once the depth of the tissue targeted for treatment is reached, the non-ablative heating of the tissue should preferably commence.

In some embodiments of the present invention, the creation of the microchannel 6 with the desired thermal affected zone profile 7 along the walls and/or bottom of the microchannel 6 may itself be the desired treatment method. Additionally or alternatively, creating the microchannel 6 itself may facilitate the desired treatment method, by providing access directly to a subcutaneous site for treatment. For example, upon completion of the microchannel, a substance may be delivered to the treatment site by any means, including for example, ultrasonic delivery. Additionally or alternatively, the microchannel may serve as a conduit for transdermal substance delivery, for example, for diffusion, electrophoresis, ointments, acids, healing substances, chemical peeling agents, collagen modification agents, fillers, stem cells, or any variety of administering medicines and the like. It will be noted that the depth of the microchannel need not be the only or even the primary treatment site; rather the treatment site may be any and all sites along the walls and/or bottom of the microchannel adjacent to or proximate the microchannel.

In some embodiments of the invention, the controller 12 may provide 3 a command via a signal 14 to the laser device for applying a pulse or series of pulses to the tissue 5. The controller may provide a variety of commands to the laser device 3, for example, the sequence and duration of pulses to apply to the tissue 5. The controller may also select form a variety of laser sources for applying a desired sequence of ablative and non-ablative laser applications to a particular site. The controller may also prescribe the desired delay between the laser applications. Furthermore, the controller 12 enables the laser emitting device 3 to deliver precise multi-spot ablation to selective portions of tissue in accordance with preselected treatment protocols as is well known by the physician.

In some embodiments, more than one microchannel may be produced substantially concurrently or in rapid sequence on the tissue 5, for example, by directing the laser emitting device 3 from one predetermined site to another of the tissue 5, applying a pulse at each site and returning precisely to the previously treated site so as to apply the next pulse in the sequence. Thus, while the tissue 5 at one microchannel is cooling, the controller 12 may send a command to the laser device 3 to move among one or more sites on the tissue 5 for creating a plurality of microchannels at a plurality of sites. Such a device may use, for example, a laser scanner. Such scanners may operate in accordance with the teachings in U.S. Pat. Nos. 5,713,902; 5,957,915; and 6,328,733, all of which are incorporated herein by reference. For example, at a first scanning sequence, the laser device 3 may provide the laser beam 4 on the first site resulting in a microchannel of depth h1. The controller 12 may then move the laser device 3 to a second site to produce thereon a microchannel having a depth h1. This process may continue until the laser device 3 performed on each location has a microchannel resulting in depth h1. The controller 12 may then proceed to provide the laser beam 4 on a microchannel site further ablating a microchannel resulting in another microchannel of depth h2 directly below the first microchannel site. Alternatively, the second laser application may be a non-ablative laser beam. The controller 12 may then move the laser device 3 to a second site to produce a microchannel of depth h2. This process may continue until the laser device 3 performed on each microchannel location of depth h1 a second laser beam pulse resulting in a microchannel of depth h2. Of course, the order of the second beam across the selected treatment sites may be in a different order or sequence than the first pass. Alternative scanning sequences may apply laser beam pulses repeatedly at a location, then moving to another location to apply laser pulses. It may not be necessary that the same series of pulses (characteristics including duration and power) be applied at each location in the sequence and any number of series of pulses may be applied to tissue at various locations.

In some embodiments of the invention, the tissue 5 may be manipulated and the laser emitting device 3 positioned for applying the laser beam 4 to the tissue 5. For example, the skin tissue to be treated may be lifted and the laser beam 4 may be applied from the side. Furthermore, the controller 12 may direct the laser emitting device 3 to apply the laser beam 3 to the tissue 5 from a variety of angles from the perpendicular.

Figure 4A:
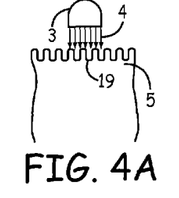
FIGS. 4A, 4B, 4C, and 4D are schematic illustrations of tissue manipulation in accordance with an embodiment of the invention.
Figures 4B, 4C:
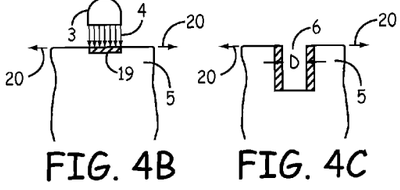
Figure 4D:
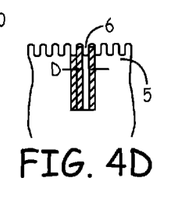

In another embodiment of the invention, it may be desirable to increase the amount of radiation per unit of surface area of the tissue 5. For example, the tissue 5 may be stretched prior to applying laser beam 4 to the tissue. Referring to FIG. 4A, laser beam 4 may be applied to unstretched tissue 5 over a surface area 19 of tissue. The tissue 5 may be stretched in a variety of directions as selected by the physician, for example, the lateral direction, manually or by some device applying a stretch 20, prior to producing the microchannel 6 as detailed above in an embodiment of the invention. Referring to FIG. 4B, applying stretch 20 to the tissue 5, effectively increases the amount of radiation per unit surface area 19 of the tissue 5. The microchannel 6 (FIG. 4C) created in the stretched tissue 5 will possess dimensions and characteristics as detailed above. Release of the tissue stretch 13, may result in a relaxed tissue 5 wherein the microchannel 6 now possesses a smaller diameter D' (i.e. D'<D; Ref. FIG. 4D). The reduction in microchannel diameter may also be a function of tissue properties, for example, tissue elasticity, tissue hydrated conditions, and the thickness of the stratum corneum. Thus, by stretching the skin prior to a laser beam is applied, the area of damaged skin may be further reduced. Stretching the skin has many advantages beyond just minimizing the amount of damaged skin. For example, by stretching the skin during the application of an ablative laser for creating a microchannel, the diameter of the microchannel will be further reduced. In this way, infection has a smaller entrance point and the chance for infection may be further minimized. Stretching the skin during the application of the laser beam (both an ablative laser beam and a non-ablative laser beam) provides additional advantages, for example, better penetration, better evacuation of vapors, and being less sensitive to the position of the target relative to the applied beam.

The system may also include an imager to enable a user to view the tissue area and to choose a treatment site. For example, the imager and an image processor may be used to determine the wrinkle topology of a tissue. For example, by using the imager combined with the application of polarized light, the outline, depth, and profile of the skin's topology may be more precisely determined. The wrinkle topology may be provided to the input interface 13 to communicate with the controller 12 and send a signal 14 to the laser device 3 to maximize the aim of the laser device 3 to the target tissue 5. The wrinkle topology may be used to measure the effectiveness of the treatment as well as used for identifying targeted sites that may require additional treatment.

In some embodiments of the invention, upon producing the microchannel and clearing a path to the treatment site, a wide variety of types of treatment may be delivered to the site, as detailed below. In some embodiments, the treatment may be non-ablative laser treatment. Such non-ablative laser treatment may be used, for example, for remodeling collagen. As is more particularly illustrated in FIG. 2D, a non-ablative laser treatment may be delivered to the tissue 5 in the dermis 9 after the microchannel 6 has been created. The path created for the non-ablative heating of the target tissue may follow embodiments of the invention detailed above regarding FIGS. 2A, or 2B and/or 2C. That is, heating of subsurface tissue by a non-ablative laser through the created microchannel may be through a microchannel that was created by one or by more than one ablative pulses. Laser treatment by the laser beam 4 may be applied to the tissue 5 in the dermis 9, whereby the tissue 5 is heated to a temperature below that at which the tissue is ablated though heated to a temperature sufficient to denature collagen, for example, in the range of from about 50.degree. C. to about 67.degree. C. The non-ablative laser beam 4 may further create a thermal affected zone of denatured collagen 17, without tissue ablation, whereby collagen is heated. The collagen thereupon contracts, thus removing wrinkles The non-ablative laser beam 4 may further be applied to targeted tissue for removing pigmentation, treating blood vessels, and other treatments, as is well known to those skilled in the art.

Figure 5:
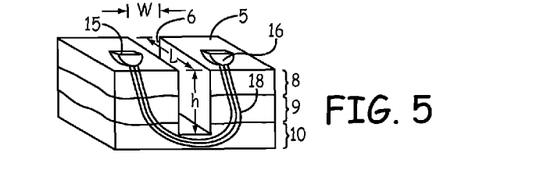
FIG. 5 is a schematic illustration of tissue treatment according to an embodiment of the invention.

As shown in FIG. 5, in another embodiment of the invention, the microchannel may be used to facilitate treatment to subcutaneous tissue by a means other than through the microchannel itself. The void of the microchannel may act as a barrier, or insulating separation of air, between layers of tissue on either side of the microchannel. Therefore, a microchannel may be used in conjunction with radio frequency (RF) energy treatment to allow driving a current below the microchannel. As illustrated, the microchannel 6 is created according to an embodiment of the present invention detailed above, having a width W, a length L, and a depth h. In this embodiment, the microchannel depth h reaches into the dermis of the tissue and the targeted tissue is beneath the microchannel 6 in the dermis 9. Radio frequency electrodes 15 and 16 may be applied to the tissue at opposite sides of the microchannel 6. When RF current 18 is applied, the insulating (non-conducting) property of the microchannel 6 requires the current to flow between electrodes 15 and 16, below the microchannel depth h, directing the current to deeper tissue than would have occurred in the absence of the microchannel 6. The length L of the microchannel should preferably be at least twice its depth (2D) so that the applied current may go through the targeted tissue and not find an alternate path of less resistance. The length of the microchannel in this embodiment of the invention may be in the range of from about 100 μm to about 500 μm, and preferably about 300 μm. Accordingly, it will be appreciated that by using the microchannels of the present invention, the heating of deeper layers of tissue may be achieved without damaging the surface tissue. It will further be appreciated that controlling the dimensions of the microchannel, e.g., the depth, width, and/or length of the microchannels may define the treatment provided by the treatment device, e.g., the RF electrodes, to the treatment layer of the tissue. It will be noted that by concentrating the current, the microchannel may provide for increased current density at the desired treatment site. A similar approach may be used for heating and followed shrinkage of collagen fibers at a predetermined depth.

Figure 6:
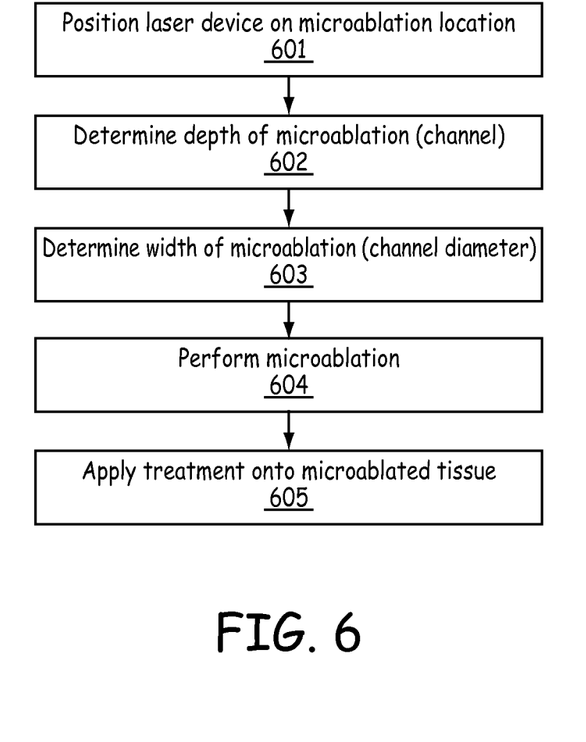
FIG. 6 is a schematic flow chart of a method of producing microablation on a tissue in accordance with an embodiment of the invention.

Creating a microchannel into the tissue for reaching an area of targeted treatment may also be achieved without an ablative laser. For example, a microchannel may be created mechanically with a heated microneedle. After the microchannel is thus formed, non-ablative treatment may be applied Reference is now made to FIG. 6, which schematically illustrates a flow-chart of a method for performing microablation on a tissue in accordance with an embodiment of the invention. As indicated at block 601, the method may include, for example, positioning the laser device for performing microchannel ablation. For example, the user of the system 1 may initially position the laser device 3 relative to the skin 5 to enable creating the microchannel at a desired location. As indicated at block 602, the method may also include, for example, determining the depth of the microchannel. For example, the user may determine that the desired depth of the microchannel 6 (FIGS. 2A, 2B and 2C) is h3. As indicated at block 603, the method may also include, for example, determining the width of the microchannel and/or the thermal affected zone. For example, the user may determine that the desired width of the microchannel 6 is D (FIG. 1) and the desired thermal affected zone profile may vary as in 7a, 7b, 7c, and 7d (FIGS. 3A, 3B, 3C and 3D). The density of microchannels (e.g., number of channels per area) can also be determined. The wavelength for the different stages of the ablation may also be determined. As indicated at block 604, the method may also include, for example, producing a microchannel. For example, the laser device 3 may emit a laser beam and may thereby produce the microchannel 6 in the tissue 5. As indicated at block 605, the method may also include, for example, applying treatment onto a microchannel location. For example, applying heat treatment to affect collagen at bottom of microchannel 6 (FIG. 2D). It will be recognized that the step of applying treatment is optional and need not be practiced in every embodiment of the invention.

Figure 7:
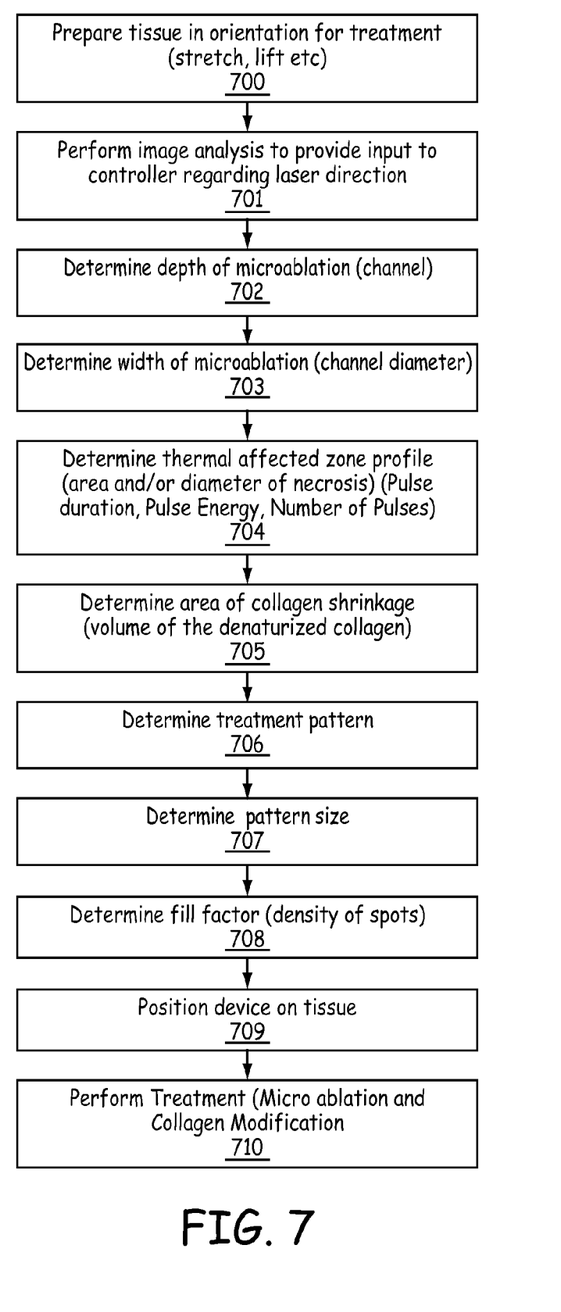
FIG. 7 is a schematic flow chart of a method of producing microablation on a tissue in accordance with an embodiment of the invention.

FIG. 7 depicts a flow chart method in accordance with embodiments of the present invention. At block 700, the orientation of the tissue 5 is selected for treatment, the tissue, e.g. skin is stretched, lifted, or left natural. At block 701, image analysis of the tissue surface is performed, for example, to create wrinkle topology, to provide information to the controller 12 (FIG. 1) in order to maximize laser orientation. It will be recognized that the step of image analysis is optional and need not be practiced in every embodiment of the invention. At blocks 702 and 703, the depth and width of the microchannels may be determined respectively, for example, based on the treatment program selected or selected by the operator. At block 704, the thermal affected zone (e.g. area and/or diameter of necrosis) may be determined, for example, by setting the pulse duration, pulse energy, the number of pulses, or the density of the pulses based on the treatment program, or based on selection by the operator. At block 705, the area of collagen shrinkage (i.e. thermal affected zone 17) may be determined (FIG. 2D). At block 706, a treatment pattern or program may be determined, for example, by the operator of the device selecting an appropriate program. At block 707, the size of the microchannel pattern may be determined, for example, automatically by scanning, or based on the treatment program, or by an operator selecting the appropriate pattern size. At block 708, the fill factor, for example, the density of the microchannels on the tissue, may be determined, for example, automatically by the device, e.g., based on the treatment program, or by selection by the operator of the device. At block 709, the device may be positioned on the tissue, and at block 710, the treatment may be performed by forming the microchannels, and/or applying any other desired treatment.

It will be appreciated by persons of ordinary skill in the art that according to some embodiments of the present invention other applications according to the principles of the present invention are possible and are in the scope of this application. While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

EXAMPLE

It is to be understood that the following example of the present invention is not intended to restrict the present invention since many more modifications may be made within the scope of the claims without departing from the spirit thereof.

A study was conducted that consisted of two research criteria. The first criterion evaluated different laser energy doses on 47 consecutive samples of skin. The doses ranged from 5 m.T to 200 mJ. The width and depth of the ablated "column" was measured as well as the surrounding width and depth of necrosis. The second criterion compared the effects of doses ranging from 5 mJ to 20 mJ on the arms of selected volunteers. These evaluations were recorded immediately after the firing of the laser; at one hour; one day and four days.

Summary of Results or Findings

The depth and diameter of the ablated columns correlated in a linear fashion with the dose. The column depth could be directly controlled and ranged from 180 to 1378 microns, depending on the dose level. Despite the wide range of dosing parameters, the column diameter was tightly confined and only ranged from 34-106 microns with most of column diameters being in the 50-70 micron range. Necrosis depth ranged from 27-213 microns. Necrosis width was extremely confined and ranged only from 19-55 microns. Histologically, the ablated columns produced by 5 mJ and 10 mJ pulses reached the mid- to deep-dermis; columns only penetrated to the fat at the highest dose (200 mJ). On doses of 5, 10, and 20 mJ, the resultant skin erythema and edema was evident at 1-2 days, but the mild to moderate erythema faded by the fourth day. There were no cases of necrosis.

Conclusions Reached

Utilizing histologic evaluation, it is a novel carbon dioxide based microablation device can produce selective digital injury to dermal collagen using very low energy levels. The collateral necrosis is very limited. Preliminary clinical evaluation using low energy doses demonstrates mild to moderate erythema that fades at four days. These findings will be used to determine the dosing for future clinical studies.

Although the particular embodiments shown and described above will prove to be useful in many applications in the skin treatment art to which the present invention pertains, further modifications of the present invention will occur to persons skilled in the art. All such modifications are deemed to be within the scope and spirit of the present invention as defined by the appended claims.

What is claimed is:

1. A method comprising:
  applying a first laser pulse to tissue for ablating a channel therein having a width and first depth, wherein the width of said channel is smaller than a treatment area in which said channel is located;
  non-ablatively heating tissue on the bottom of said channel with a second laser pulse
  to create a thermal affected zone having a volume proximate said channel; and
  applying a third laser pulse to the bottom of said channel to ablate said channel through the thermal affected zone to a second depth.

2. The method of claim 1, further comprising applying electromagnetic radiation to tissue through said channel for creating a second thermal affected zone having a volume proximate said channel.

3. The method of claim 1, further comprising:
  creating a second thermal affected zone of predetermined volume and profile proximate said channel.

4. The method of claim 1, further comprising administering a treatment through said channel.

5. The method of claim 2, wherein said electromagnetic radiation comprises elevating the temperature of the tissue to less than about 100° C.

6. The method of claim 1, wherein said first laser pulse comprises a series of pulses.

7. The method of claim 1, wherein said thermal affected zone comprises a non-uniform volume along the depth of said channel.

8. The method of claim 1, wherein said thermal affected zone comprises a non-uniform profile along the depth of said channel.

9. The method of claim 1, further comprising increasing the amount of radiation per unit of surface area of the tissue prior to applying said first laser pulse by stretching the skin.

* * * * *